(12) United States Patent
Hatase et al.

(10) Patent No.: US 10,167,304 B2
(45) Date of Patent: Jan. 1, 2019

(54) RUTHENIUM COMPOUND, MATERIAL FOR THIN FILM FORMATION, AND PROCESS FOR THIN FILM FORMATION

(71) Applicant: ADEKA CORPORATION, Tokyo (JP)

(72) Inventors: Masako Hatase, Tokyo (JP); Masaki Enzu, Tokyo (JP); Atsushi Sakurai, Tokyo (JP); Tomoharu Yoshino, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 316 days.

(21) Appl. No.: 15/032,230

(22) PCT Filed: Nov. 7, 2014

(86) PCT No.: PCT/JP2014/079576
§ 371 (c)(1),
(2) Date: Apr. 26, 2016

(87) PCT Pub. No.: WO2015/093177
PCT Pub. Date: Jun. 25, 2015

(65) Prior Publication Data
US 2016/0272664 A1  Sep. 22, 2016

(30) Foreign Application Priority Data

Dec. 20, 2013  (JP) ................ 2013-264576

(51) Int. Cl.
| C07F 15/00 | (2006.01) |
| C07C 225/14 | (2006.01) |
| C23C 16/16 | (2006.01) |
| C23C 16/455 | (2006.01) |

(52) U.S. Cl.
CPC ........ *C07F 15/0046* (2013.01); *C07C 225/14* (2013.01); *C23C 16/16* (2013.01); *C23C 16/45553* (2013.01)

(58) Field of Classification Search
CPC .................................. C07F 15/0046
USPC ....................................... 544/64
See application file for complete search history.

(56) References Cited

U.S. PATENT DOCUMENTS

| 5,008,415 A | 4/1991 | Norman |
| 6,316,064 B1 | 11/2001 | Onozawa et al. |
| 6,743,934 B2 | 6/2004 | Saito et al. |
| 8,642,796 B2 | 2/2014 | Saito et al. |
| 2003/0203102 A1 | 10/2003 | Saito et al. |
| 2011/0318488 A1 | 12/2011 | Saito et al. |

FOREIGN PATENT DOCUMENTS

| JP | 2000-212744 | 8/2000 |
| JP | 2003-306472 | 10/2003 |
| JP | 2012-006858 | 1/2012 |
| JP | 2013-253035 | 12/2013 |
| JP | 2013253035 | * 12/2013 |
| WO | WO 2010/071364 | 6/2010 |

OTHER PUBLICATIONS

International Search Report, PCT/JP2014/079576, dated Feb. 3, 2015.
Zharkova, G. I. et al., O,N-coordinated Ni(II) beta-diketonate derivatives: Synthesis, thermal properties, MOCVD applications, Surface & Coatings Technology, Sep. 15, 2013, vol. 230, p. 290-296.
Chou, T.-Y. et al., Synthesis and characterization of tris(B-ketoiminato) ruthenium(III) complexes: Potential precursors for CVD of Ru and RuO2 thin films, Chemical Vapor Deposition, 2004, vol. 10, No. 3, p. 149-158.
Rees, W. S., Jr. et al., Synthesis and magnetic and structural characterization of the first homoleptic lanthanide B-ketoiminate, Inorganic Chemistry, 2000, vol. 39, p. 3736-3737.

* cited by examiner

*Primary Examiner* — Charanjit Aulakh
(74) *Attorney, Agent, or Firm* — Young & Thompson (57) ABSTRACT

Disclosed is a ruthenium compound useful as a precursor in chemical vapor growth, particularly ALD. The compound has good reactivity with a reactive gas, a high vapor pressure, and a low melting point. The compound is represented by general formula (I), wherein $R^1$, $R^2$, and $R^3$ each independently represent a straight or branched chain alkyl group having 1 to 5 carbon atoms, provided that the total number of the carbon atoms of $R^1$ and $R^2$ is 3 to 10. In formula (I), $R^1$ and $R^2$ are each preferably ethyl or isopropyl.

7 Claims, 3 Drawing Sheets

RUTHENIUM COMPOUND, MATERIAL FOR THIN FILM FORMATION, AND PROCESS FOR THIN FILM FORMATION

TECHNICAL FIELD

This invention relates to a novel ruthenium compound having a specific structure, a material for thin film formation containing the ruthenium compound, and a process for forming a ruthenium-containing thin film using the material.

BACKGROUND ART

A ruthenium-containing material for thin film formation exhibits specific electric characteristics and has found wide applications. For example, a ruthenium thin film has been used as an electrode of memory devices typified by DRAM devices, a resistant film, a diamagnetic film used in the recording layer of hard disks, and a catalyst for polymer electrolyte fuel cells.

Processes for forming the above-described thin film include sputtering, ion plating, MOD techniques such as a dipping-pyrolysis process and a sol-gel process, and chemical vapor growth techniques. Chemical vapor growth techniques (hereinafter abbreviated as CVD) including atomic layer deposition (ALD) is the most suitable for many advantages, such as compositional controllability, excellent step coverage, suitability to large volume production, and capability of hybrid integration.

Various ruthenium compounds are known as raw materials for CVD. For example, Patent Literature 1 below discloses a ruthenium compound having two carbonyl groups and two ketoimine groups having a specific structure but does not mention about the ruthenium compound of the present invention. The ruthenium compound of Patent Literature 1 is not sufficiently satisfactory as a material for CVD because of its melting point of 100° C. or higher.

CITATION LIST

Patent Literature

Patent Literature 1: WO2010/071364

SUMMARY OF THE INVENTION

Problem to be Solved by the Invention

Properties required of a compound (precursor) suited as a raw material for thin film formation involving vaporization of the compound, such as CVD, are a low melting temperature (to be transportable in liquid form), a low liquid viscosity, a high vapor pressure (vaporizability), and high thermal stability. For application to ALD, in particular, good reactivity with a reactive gas is demanded. In particular, a ruthenium compound applied to ALD is required to have good reactivity with a reactive gas, a high vapor pressure, and a low melting point. There is no conventional ruthenium compound that sufficiently meets these requirements.

Means to Solve the Problem

As a result of extensive investigations, the inventors have found that the above problem is solved by a ruthenium compound having a specific structure and reaches the present invention.

The invention provides a ruthenium compound represented by general formula (I):

[Chem.1]

wherein $R^1$, $R^2$, and $R^3$ each independently represent a straight or branched chain alkyl group having 1 to 5 carbon atoms, provided that the total number of the carbon atoms of $R^1$ and $R^2$ is 3 to 10.

The invention also provides a material for thin film formation containing the ruthenium compound of general formula (I).

The invention also provides a process for forming a thin film including vaporizing the material for thin film formation and introducing the resulting vapor containing the ruthenium compound into a deposition chamber having a substrate placed therein to cause the ruthenium compound to decompose and/or chemically react to form a ruthenium-containing thin film on the substrate.

Effect of the Invention

The invention provides a ruthenium compound having good reactivity with a reactive gas, a low melting point, sufficient volatility, and high thermal stability. The ruthenium compound is suitable as a material for thin film formation by CVD. It is especially suited as a material for thin film formation by ALD because of its satisfactory reactivity with a reactive gas typified by hydrogen.

BRIEF DESCRIPTION OF THE INVENTION

EMBODIMENTS FOR CARRYING OUT THE INVENTION

The invention will be described in detail generally based on its preferred embodiments.

The ruthenium compound of the invention is represented by general formula (I). It is suitable as a precursor used in thin film formation including a vaporization step, such as CVD. It is particularly suitable as a precursor for use in ALD because of its good reactivity with a reactive gas and high thermal stability.

Examples of the C1-C5 straight or branched chain alkyl group as represented by $R^1$, $R^2$, and $R^3$ include methyl, ethyl, propyl, isopropyl, butyl, sec-butyl, tert-butyl, isobutyl, pentyl, sec-pentyl, tert-pentyl, isopentyl, and neopentyl. The total number of the carbon atoms of $R^1$ and $R^2$ is 3 to 10.

$R^1$, $R^2$, and $R^3$ in general formula (I) are selected as appropriate to the thin film formation process to which the compound is applied. In the case where the compound of general formula (I) is used in a thin film formation process including the step of vaporizing the compound, $R^1$, $R^2$, and $R^3$ in formula (I) are preferably selected so that the compound is liquid and has a high vapor pressure at ambient temperature and ambient pressure. Specifically, the compounds in which the total number of the carbon atoms of $R^1$ and $R^2$ is 3 to 8 are preferred for their low melting point, and the compounds in which the total number of the carbon atoms is 3 to 6 are more preferred for their particularly low melting point. Inter alia, those in which $R^1$ is methyl and $R^2$ is ethyl, those in which $R^1$ and $R^2$ are each ethyl, and those in which $R^1$ and $R^2$ are each isopropyl are especially preferred because they stably maintain the liquid state in the atmosphere at 25° C.

The compounds in which $R^3$ is methyl, ethyl, propyl, or isopropyl are preferred for their low melting point and high vapor pressure. Inter alia, those in which $R^3$ is methyl or ethyl are preferred for their particularly low melting point.

In the case when the compound is used for an MOD process involving no vaporization step, $R^1$, $R^2$, and $R^3$ may be selected as appropriate to the solubility in a solved used, the thin film formation reaction, and the like.

Preferred examples of the ruthenium compounds of the invention include compound Nos. 1 through 14 given below. In the structural formulae below, Me is methyl, Et is ethyl, iPr is isopropyl, sBu is sec-butyl, tBu is tert-butyl, and tAm is tert-pentyl.

[Chem.2A]

Compound No.1 lp;1p

Compound No.2

Compound No.3

Compound No.4

Compound No.5

Compound No.6

Compound No.7

Compound No.8

Compound No.9

[Chem.2B] -continued

Compound No.10

Compound No.11

Compound No.12

Compound No.13

Compound No.14

The ruthenium compound of the invention is not limited by the method of preparation and may be prepared making use of known reactions. For example, the compound of the invention can be obtained by allowing a carbonyl ruthenium compound, typified by triruthenium dodecacarbonyl, to react with a ketoimine compound the structure of which corresponds to the compound to be prepared.

The thin film forming material according to the invention contains the ruthenium compound of the invention as a thin film precursor and may have a form appropriate to the process to which the material is applied. For example, in forming a thin film containing ruthenium as a sole metal, the thin film forming material of the invention is free of a metal or semimetal compound other than the ruthenium compound of the invention. In forming a thin film containing ruthenium and a metal other than ruthenium and/or a semimetal, the thin film forming material of the invention contains, in addition to the ruthenium compound of the invention, a compound containing the metal other than ruthenium and/or a compound containing the semimetal (hereinafter inclusively referred to as (an)other precursor(s)). When the thin film forming material contains another precursor, the content of the other precursors in the material is preferably 0.01 to 10 mol, more preferably 0.1 to 5 mol, per mole of the ruthenium compound of the invention. The thin film forming material of the invention may further contain an organic solvent and/or a nucleophilic reagent as will be described later.

Since the ruthenium compound (precursor) of thin film forming material of the invention has physical properties suitable to CVD and ALD as previously discussed, the thin film forming material is particularly useful as a material for chemical vapor growth (hereinafter also called a CVD material).

For use as a CVD material, the thin film forming material of the invention may have a form selected as appropriate for the CVD system adopted, such as a source delivery system.

The source delivery system is exemplified by a vapor delivery system in which a CVD material is vaporized by heating and/or pressure reduction in a source container and introduced into a deposition chamber (sometimes referred to as a reaction chamber) having a substrate placed therein, if desired, together with a carrier gas, e.g., argon, nitrogen or helium, and a liquid delivery system in which a CVD material is delivered in the form of a liquid or a solution to a vaporizer, where it is vaporized by heating and/or pressure reduction and then introduced to a deposition chamber. When applied to the vapor delivery system, the ruthenium compound represented by general formula (I) per se is the CVD material. In the case of the liquid delivery system, the ruthenium compound of general formula (I) per se or a solution of the compound in an organic solvent is the CVD material.

In a multi-component CVD process, the source delivery systems include a system in which a plurality of precursors are separately vaporized and delivered (hereinafter referred to as a multi-source system) and a system in which a plurality of the precursors are previously mixed at a prescribed ratio, and the mixture is vaporized and delivered (hereinafter referred to as a single source system). In the case of the single source system, the CVD material may be a mixture or mixed solution containing the ruthenium compound of the invention or a mixture or mixed solution containing the ruthenium compound of the invention and other precursor(s).

The organic solvent that can be used in the CVD material is not particularly limited, and any widely known organic solvent may be used. Examples of useful organic solvents include acetic esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent or a mixture of solvents to be used is selected according to, for example, solubility of the solute and the boiling temperature or ignition temperature in relation to the working temperature. In using these organic solvents, the total concentration of the ruthenium compound of the invention and the other precursor(s) in the organic solvent is preferably 0.01 to 2.0 mol/l, more preferably 0.05 to 1.0 mol/l.

The other precursors that can be used in combination with the ruthenium compound of the invention in multi-component CVD are not particularly limited, and compounds known as precursors used in CVD materials are useful.

Examples of the other precursors include compounds formed between silicon or a metal except ruthenium and at least one compound selected from the group consisting of organic coordinating compounds, such as alcohol compounds, glycol compounds, β-diketone compounds, cyclopentadiene compounds, organic amine compounds, and ketoimine compounds. The metal species of the other precursors include magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

Examples of the alcohol compounds that can be used as an organic ligand of the other precursors include alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxy) ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; and amino alcohols, such as 1-methylamino-2-propanol, 1-ethylmethylamino-2-propanol, 1-diethylamino-2-propanol, 1-dimethylamino-2-methyl-2-propanol, 1-ethylmethylamino-2-methyl-2-propanol, 1-diethylamino-2-methyl-2-propanol, 1-dimethylamino-2-butanol, 1-ethylmethylamino-2-butanol, 1-diethylamino-2-butanol, 1-dimethylamino-2-methyl-2-butanol, 1-ethylmethylamino-2-methyl-2-butanol, and 1-diethylamino-2-methyl-2-butanol.

Examples of the glycol compounds include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compounds include alkyl-substituted β-diketones, such as acetylacetone, hexane-2,4-dione, 5-methylhexane-2,4-dione, heptane-2,4-dione, 2-methylheptane-3,5-dione, and 2,6-dimethylheptane-3,5-dione; fluoroalkyl-substituted β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compounds include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene. Examples of the organic amine compounds include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, isopropylmethylamine, ethylenediamine, and N,N-dimethylethylenediamine Examples of the ketoimine compounds include reaction products between the above described β-diketone compound and the above described organic amine compound, such as a ketoimine compound obtained by the reaction between acetylacetone and N,N-dimethylethylenediamine in the presence of hydrogen chloride.

In the case of the multi-source system, it is preferred that the other precursors be similar to the ruthenium compound of the invention in thermal and/or oxidative decomposition behavior. In the case of a single-source system, it is preferred that the other precursors be similar to the ruthenium compound of the invention in thermal and/or oxidative decomposition behavior and, in addition, not alter in properties due to chemical reaction on mixing.

Of the above described other precursors those containing titanium, zirconium, or hafnium include compounds represented by general formulae (II-1) to (II-5):

[Chem. 3]

(II-1)

(II-2)

(II-3)

(II-4)

(II-5)

In the formula, $M^1$ represents titanium, zirconium, or hafnium, $R^a$ and $R^b$ each independently represent a $C_{1-20}$ alkyl group that may be substituted by a halogen atom and that may include an oxygen atom in its chain, $R^c$ represents a $C_{1-8}$ alkyl group, $R^d$ represents a $C_{2-18}$ alkylene group that may be branched, $R^e$ and $R^f$ each independently represent a hydrogen atom or a $C_{1-3}$ alkyl group, $R^g$, $R^h$, $R^k$, and $R^j$ each independently represent a hydrogen atom or a $C_{1-4}$ alkyl group, p represents an integer of 0 to 4, q represents 0 or 2, r represents an integer of 0 to 3, s represents an integer of 0 to 4, and t represents an integer of 1 to 4.

In general formulae (II-1) to (II-5), examples of the C1-C20 alkyl group optionally substituted with a halogen atom and optionally containing an oxygen atom in its chain as represented by $R^a$ and $R^b$ include methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. Examples of the C1-C8 alkyl group represented by $R^c$ include methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl. The optionally branched C2-C18 alkylene group represented by $R^d$ is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the C1-C3 alkyl group represented by $R^e$ and $R^f$ include methyl, ethyl, propyl, and 2-propyl. Examples of the C1-C4 alkyl represented by $R^g$, $R^h$, $R^j$, and $R^k$ include methyl, ethyl, propyl, isopropyl, butyl, sec-butyl, tert-butyl, and isobutyl.

Examples of the precursors containing titanium include tetrakisalkoxytitaniums, such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium, and tetrakis(1-methoxy-2-methyl-2-propoxy)titanium; tetrakis(β-diketonato)titaniums, such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titaniums, such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; glycoxybis(β-diketonato)titaniums, such as (2-methylpentanedioxy)bis(2,2,6,6-tetramethylheptane-3,5-dionato)titanium and (2-methylpentanedioxy)bis(2,6-dimethylheptane-3,5-dionato)titanium; cyclopentadienyltris(dialkylamino)titaniums, such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; and (cyclopentadienyl)tris(alkoxy)titaniums, such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl)tris(methoxy)titanium, and (tert-butylcyclopentadienyl)tris(methoxy)titanium.

Examples of the precursors containing zirconium or precursors containing hafnium include the above-listed titanium precursors with titanium displaced with zirconium or hafnium.

Examples of the precursors containing a rare earth element include compounds represented by general formulae (III-1) to (III-3):

[Chem. 4]

In the formula, $M^2$ represents a rare-earth atom, $R^a$ and $R^b$ each independently represent a $C_{1-20}$ alkyl group that may be substituted by a halogen atom and that may include an oxygen atom in its chain, $R^c$ represents a $C_{1-8}$ alkyl group, $R^e$ and $R^f$ each independently represent a hydrogen atom or a $C_{1-3}$ alkyl group, $R^g$ and $R^j$ each independently represent a $C_{1-4}$ alkyl group, p' represents an integer of 0 to 3, and r' represents an integer of 0 to 2.

Examples of the rare earth element represented by $M^2$ in general formulae (III-1) to (III-3) include scandium, yttrium, lanthanum, cerium, praseodymium, promethium, samarium, europium, gadolinium, terbium, dysprosium, holmium, erbium, thulium, ytterbium, and lutetium. Examples of the groups represented by $R^a$, $R^b$, $R^c$, $R^e$, $R^f$, $R^g$, and $R^j$ include those enumerated for the titanium-containing precursors.

If desired, the thin film forming material of the invention may contain a nucleophilic reagent to stabilize the ruthenium compound of the invention and other precursors. Examples of useful nucleophilic reagents include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, and 3,5-heptanedione. The nucleophilic reagent is used usually in an amount of 0.1 to 10 mol, preferably 1 to 4 mol, per mole of the precursor(s).

The thin film forming material of the invention should have minimized contents of impurities other than the constituent components, including impurity metal elements, impurity halogens (e.g., impurity chlorine), and impurity organic matter. The impurity metal element content is preferably 100 ppb or less, more preferably 10 ppb or less, for every element, and a total impurity metal content is preferably 1 ppm or less, more preferably 100 ppb or less. In particular, in the fabrication of a thin film for use as a gate insulator film, a gate film, or a barrier film of LSI devices, it is required to minimize the contents of alkali metal elements, alkaline earth metal elements, and congeneric elements that are influential on the electrical characteristics of the resulting thin film. The impurity halogen content is preferably 100 ppm or less, more preferably 10 ppm or less, even more preferably 1 ppm or less. The total impurity organic matter content is preferably 500 ppm or less, more preferably 50 ppm or less, even more preferably 10 ppm or less. A water content causes particle generation in the chemical vapor growth material or during thin film formation. Therefore, it is advisable to previously remove the water content from the metal compound, the organic solvent, and the nucleophilic reagent as much as possible before use. The water content of each of the metal compound, organic solvent, and nucleophilic reagent is preferably 10 ppm or less, more preferably 1 ppm or less.

In order to reduce or prevent contamination of a thin film with particles, it is desirable for the thin film forming material of the invention to have minimized particles. Specifically, it is desirable for the material to have not more than 100 particles greater than 0.3 µm, more desirably not more than 1000 particles greater than 0.2 µm, even more desirably not more than 100 particles greater than 0.2 µm, per ml of its liquid phase as measured with a light scattering particle sensor for detecting particles in a liquid phase.

The process for forming a thin film according to the present invention, which is characterized by using the above described thin film forming material of the invention, includes vaporizing the ruthenium compound of the invention and, if necessary, other precursors, introducing the vapor and, if necessary, a reactive gas to a deposition chamber having a substrate placed therein, and causing the precursor to decompose and/or chemically react to grow and deposit a thin film on the substrate (CVD process). The process is not particularly restricted by the material delivery system, the mode of deposition, the film formation conditions and equipment, and the like. Any conditions and methods commonly known in the art may be used.

Examples of the reactive gas that may be used if necessary include oxidizing gases, such as oxygen, ozone, nitrogen dioxide, nitrogen monoxide, water vapor, hydrogen peroxide, formic acid, acetic acid, and acetic anhydride; and reducing gases, such as hydrogen. Reactive gases that can be used to form a nitride film include organic amine compounds, such as monoalkylamines, dialkylamines, trialkylamines, and alkylenediamines; hydrazine and ammonia. These reactive gases may be used either individually or in combination of two or more thereof.

The material delivery systems include the above-described vapor delivery system, liquid delivery system, single source system, and multi-source system.

The deposition modes include thermal CVD (only heat is used to cause the vaporized material or the vaporized material and a reactive gas to react to deposit a film), plasma-enhanced CVD (heat and plasma are used), photo-assisted CVD (heat and light are used), photo plasma-assisted CVD (heat, light, and plasma are used), and ALD in which a deposition reaction of CVD is divided into elementary reaction steps so as to build up a film stepwise on a molecular level.

The film formation conditions as referred to above include reaction temperature (substrate temperature), reaction pressure, and deposition rate. The reaction temperature is preferably 100° C. or higher at which the ruthenium compound of the invention and other reactants react sufficiently, more preferably 150° to 400° C. The reaction pressure is from atmospheric pressure to 10 Pa for thermal CVD and photo-assisted CVD or from 10 to 2000 Pa for film formation using plasma.

The deposition rate can be controlled by the material feed conditions (vaporizing temperature and vaporizing pressure) and the reaction temperature and pressure. Too high a deposition rate tends to result in deteriorated characteristics of the resulting thin film, and too low a deposition rate can result in poor productivity. A preferred deposition rate ranges from 0.01 to 100 nm/min, more preferably 1 to 50 nm/min. In the case of ALD, the film thickness is controlled by the number of cycles to reach a desired film thickness.

Formation of, for example, a metallic ruthenium thin film by an ALD process is carried out as follows. After the above-described source delivery (pulse step), the ruthenium compound pulsed into a reaction chamber is deposited on the substrate to form a precursor monolayer (precursor monolayer formation step). During the precursor monolayer formation step, heat may be applied by heating the substrate or the reaction chamber. The precursor monolayer formed in this step is a metallic ruthenium thin film or a thin film formed by the decomposition and/or reaction of part of the ruthenium compound and is different in composition from the desired metallic ruthenium thin film. The substrate temperature in this step is preferably room temperature to 500° C.

The unreacted ruthenium compound gas and by-produced gas are purged out of the reaction chamber (purging step). Although it is ideal for the unreacted ruthenium compound gas and by-produced gas to be purged out completely, they do not always have to be. The purging may be achieved by, for example, purging the chamber with an inert gas, such as nitrogen, helium, or argon; evacuating the chamber by reducing the inner pressure; or a combination thereof. The degree of vacuum to be reached by the evacuation is preferably 0.01 to 300 Pa, more preferably 0.01 to 100 Pa.

A reactive gas is then pulsed into the reaction chamber and allowed to react with the precursor monolayer with or without heat application to form a monolayer of metallic ruthenium (metallic ruthenium monolayer formation step). The temperature of the heat, if applied in this step, is preferably room temperature to 500° C., more preferably 150° to 350° C. The ruthenium compound of the invention exhibits good reactivity with a reactive gas typified by oxygen to form a metallic ruthenium thin film.

In the case of using an ALD process to form a thin film, the above described series of pulse step, precursor monolayer formation step, purging step, and metallic ruthenium monolayer formation step makes one cycle, which may be repeated until a desired film thickness is reached. In that case, it is preferred that every cycle be followed by purging the unreacted ruthenium compound gas and the reactive gas and the by-produced gas out of the reaction chamber.

In carrying out metallic ruthenium thin film formation by ALD, energy such as plasma, light, or electric voltage may be applied. The stage of energy application is not particularly limited. The energy may be applied at the time of introducing the ruthenium compound gas in the pulse step, at the time of heating in the precursor monolayer formation step or the metallic ruthenium monolayer formation step, at the time of purging the chamber in the purging step, at the time of introducing the reactive gas in the metallic ruthenium monolayer formation step, or between any two of the steps.

In the film formation process of the invention, the deposited thin film may be subjected to annealing in an inert atmosphere, an oxidative atmosphere, or a reducing atmosphere to obtain improved electrical characteristics. Where step coverage is required, the process may include the step of reflowing the thin film. The temperature for reflowing is usually from 200° to 1000° C., preferably 250° to 500° C.

Figure 1:
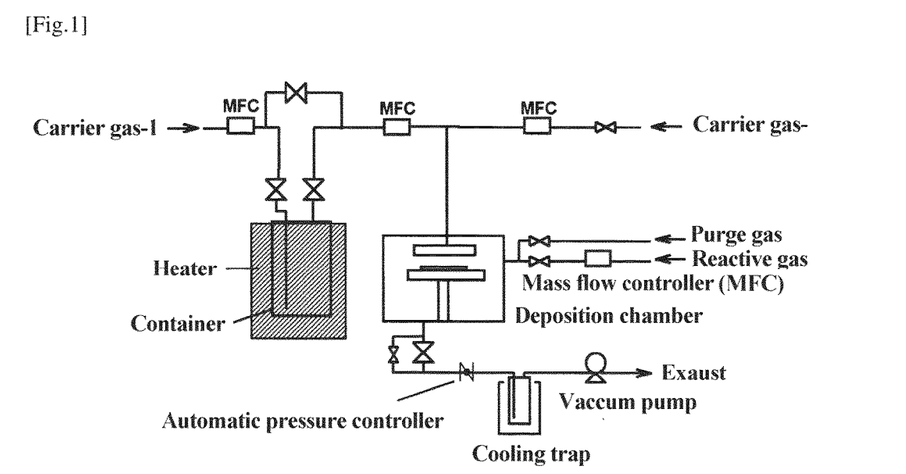
FIG. 1 is a schematic illustration of an example of an apparatus for chemical vapor growth that can be used to carry out the process for forming a ruthenium-containing thin film according to the invention.
Figure 2:
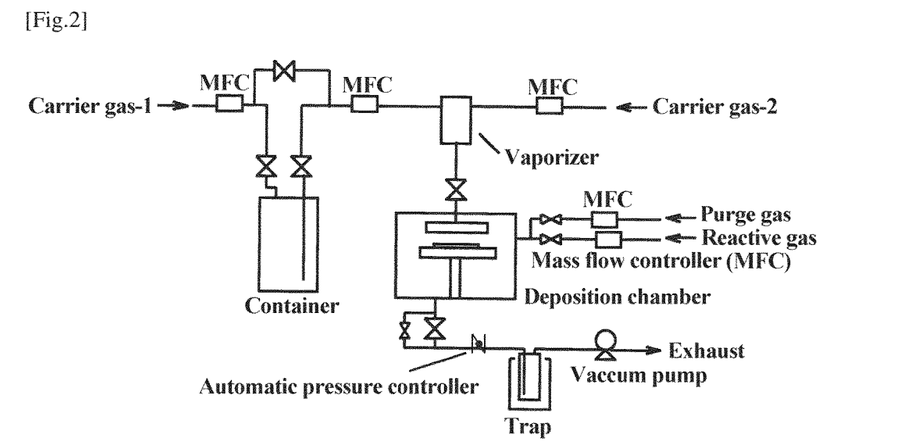
FIG. 2 is a schematic illustration of another example of an apparatus for chemical vapor growth that can be used to carry out the process for forming a ruthenium-containing thin film according to the invention.
Figure 3:
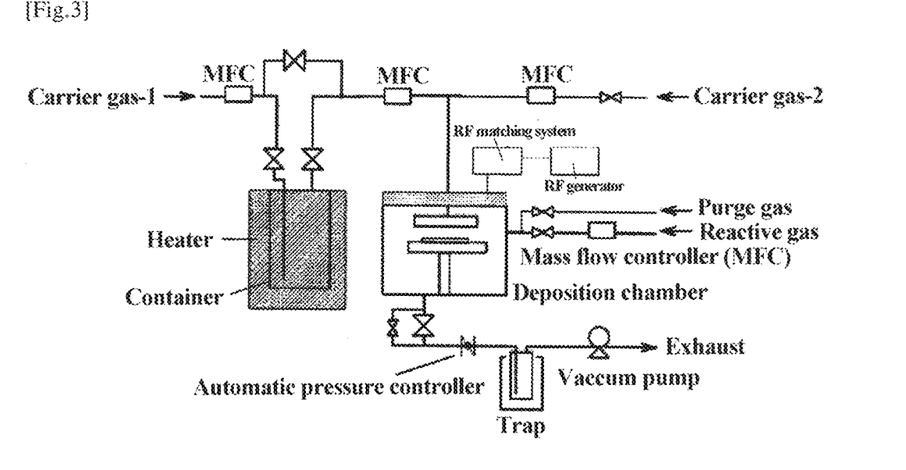
FIG. 3 is a schematic illustration of still another example of an apparatus for chemical vapor growth that can be used to carry out the process for forming a ruthenium-containing thin film according to the invention.
Figure 4:
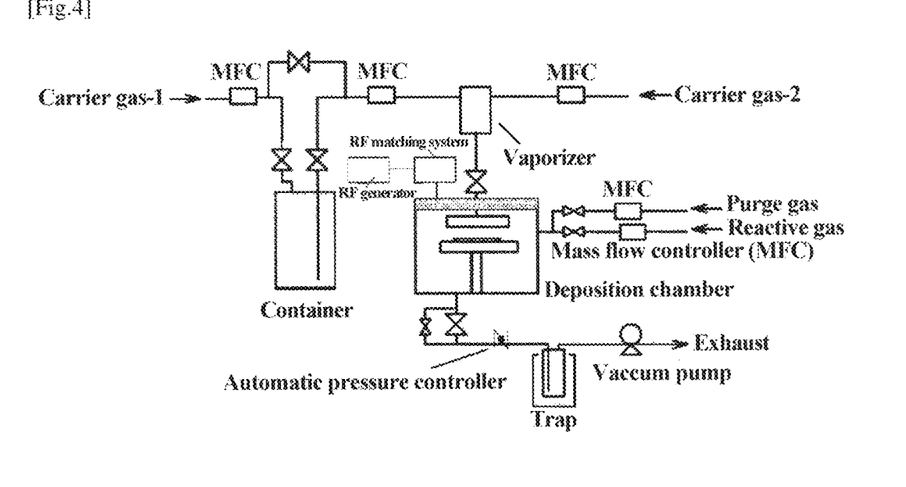
FIG. 4 is a schematic illustration of yet another example of an apparatus for chemical vapor growth that can be used to carry out the process for forming a ruthenium-containing thin film according to the invention.

Known equipment for chemical vapor growth can be used to carry out thin film formation using the thin film forming material of the invention. Examples of useful equipment include an apparatus capable of introducing a precursor by a bubbler delivery system as illustrated in FIG. 1, an apparatus having a vaporizer as illustrated in FIG. 2, and an apparatus capable of treating a reactive gas with plasma as illustrated in FIGS. 3 and 4. Not only single-substrate type apparatuses like those shown in FIGS. 1 through 4 but batch type apparatuses capable of treating a plurality of substrates in a single chamber are also used.

Combined with appropriate selections of other precursors, a reactive gas, and film forming conditions, the thin film forming material of the invention provides a thin film of desired kind, such as metals, oxide ceramics, nitride ceramics, and glass. The thin films produced by the invention include a metallic ruthenium thin film, a ruthenium oxide thin film, and a ruthenium alloy or double or complex ruthenium oxide thin film. Examples of the ruthenium alloy include a Pt—Ru alloy. Examples of the double or complex ruthenium oxide are $SrRuO_3$. These thin films are widely used as an electrode of memory devices typified by DRAM devices, a resistant film, a diamagnetic film used in the recording layer of hard disks, and a catalyst for polymer electrolyte fuel cells.

EXAMPLES

The present invention will now be illustrated in greater detail with reference to Examples and Evaluation Examples, but it should be understood that the invention is not construed as being limited thereto.

Example 3—Preparation of Compound No. 3

Figure 5:
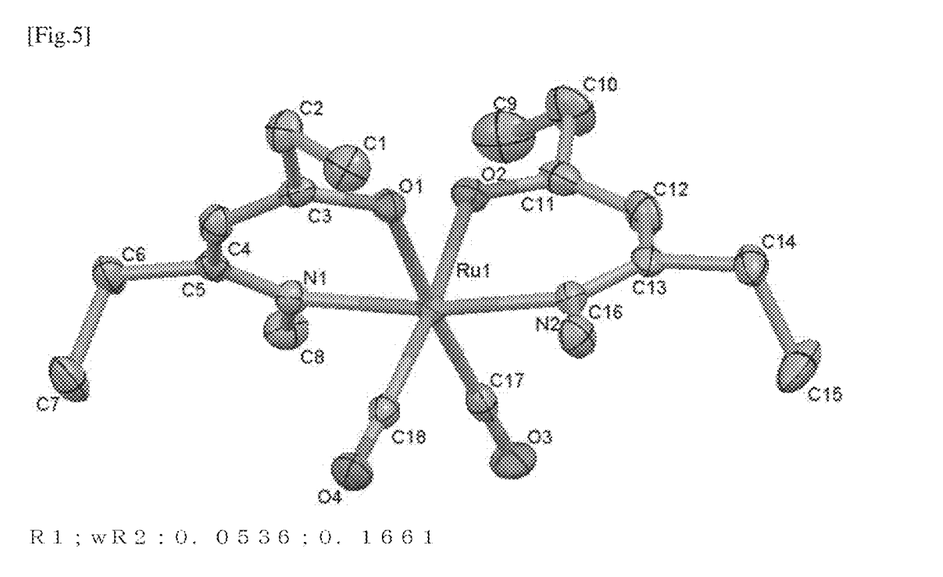
FIG. 5 is the molecular structure of compound No. 3 determined by X-ray single crystal structural analysis.

In an argon atmosphere, 2.0 g (3.13 mmol) of $Ru_3(CO)_{12}$, 100 ml of decane, and 2.9 g (20.5 mmol) of 5-methylamino-4-hepten-3-one were mixed and stirred at a water bath temperature of 130° C. under atmospheric pressure for 31.5 hours. After allowing the mixture to cool to room temperature, the mixture was filtered using a G2 ball filter to obtain a yellow filtrate. The filtrate was evaporated at a bath temperature of 110° C. under reduced pressure to remove decane to give an orange liquid, which was distilled at 130° C. under reduced pressure using a glass tube oven to furnish 1.7 g (yield: 44%) of compound No. 3 as a yellow solid (melting point: 54° C.). The product was analyzed by (1) ambient-pressure TG-DTA, (2)$^1$H-NMR, and (3) DSC. The results are described below. The product was also analyzed by X-ray single crystal structural analysis, the results of which are depicted in FIG. 5.

Analytical Values:
(1) Ambient-Pressure TG-DTA
Fifty percent mass loss temperature: 239° C. (Ar flow rate: 100 ml/min; rate of temperature rise: 10° C./min)
(2)$^1$H-NMR (Solvent: Deuterobenzene) (Chemical Shift: Multiplicity:Proton Ratio) (0.799-0.837:t:6) (1.165-1.202:t:6) (1.843-1.971:m:4) (2.225-2.283:m:4) (3.336:s:6) (4.820:s:2)
(3) DSC (Sample Weight: 1.93 mg; Rate of Temperature Rise: 10.0° C./Min) 340° C.

Example 2—Preparation of Compound No. 4

In an argon atmosphere, 1.36 g (2.13 mmol) of $Ru_3(CO)_{12}$, 75 ml of decane, and 2.08 g (13.4 mmol) of 5-ethylamino-4-hepten-3-one were mixed and stirred at a water bath temperature of 128° C. under atmospheric pressure for 21.5 hours. After allowing the mixture to cool to room temperature, the mixture was filtered using a G2 ball filter to obtain an orange filtrate. The filtrate was evaporated at a bath temperature of 118° C. under reduced pressure to remove decane to give an orange liquid, which was distilled at 125° C. under reduced pressure using a glass tube oven to afford 0.85 g (yield: 28%) of compound No. 4 as an orange liquid. The product was analyzed by (1) ambient-pressure TG-DTA, (2)$^1$H-NMR, and (3) DSC. The results are described below.

Analytical Values:
(1) Ambient-Pressure TG-DTA
Fifty percent mass loss temperature: 245° C. (Ar flow rate: 100 ml/min; rate of temperature rise: 10° C./min)
(2)$^1$H-NMR (Solvent: Deuterobenzene) (Chemical Shift: Multiplicity:Proton Ratio)
(0.897-0.935:t:6) (1.144-1.182:t:6) (1.174-1.210:t:6) (1.837-1.889:m:2) (1.955-2.007:m:2) (2.207-2.265:m:4) (3.558-3.610:m:2) (3.805-3.857:m:2) (4.776:s:s)
(3) DSC (Sample Weight: 6.62 mg; Rate of Temperature Rise: 10.0° C./Min) 300° C.

Example 3—Preparation of Compound No. 8

In an argon atmosphere, 2.04 g (3.18 mmol) of $Ru_3(CO)_{12}$, 115 ml of decane, and 3.68 g (20.1 mmol) of 5-ethylamino-2,6-dimethyl-4-hepten-3-one were mixed and stirred in at a bath temperature of 140° C. under atmospheric pressure for 24 hours. After allowing the mixture to cool to room temperature, the mixture was filtered using a G2 ball filter to obtain a yellow filtrate. The filtrate was evaporated at a bath temperature of 77° C. under reduced pressure to remove decane to give an orange liquid, which was distilled at 125° C. under reduced pressure using a glass tube oven to afford 1.1 g (yield: 22%) of compound No. 8 as a transparent viscous yellow liquid. The product was analyzed by (1)

ambient-pressure TG-DTA, (2) reduced-pressure TG-DTA, (3)$^1$H-NMR, and (4) DSC. The results are described below.
Analytical Values:
(1) Ambient-pressure TG-DTA Fifty percent mass loss temperature: 240° C. (Ar flow rate: 100 ml/min; rate of temperature rise: 10° C./min)

(2) Reduced-Pressure TG-DTA

Fifty percent mass loss temperature: 154° C. (10 Torr; Ar flow rate: 50 ml/min; rate of temperature rise: 10° C./min)

(3)$^1$H-NMR (Solvent: Deuterobenzene) (Chemical Shift: Multiplicity:Proton Ratio)

(0.947-0.971:dd:6) (1.129-1.147:d:12) (1.173-1.190:d:12) (2.431-2.500:sept:2) (2.755-2.805:sept:2) (3.597-3.649:m:2) (3.865-3.935:m:2) (4.894:s:2)

(4) DSC (Sample Weight: 1.93 mg; Rate of Temperature Rise: 10.0° C./Min) 290° C.

Evaluation Example 1—Evaluation of Melting Point

The state of compound Nos. 3, 4, and 8 obtained in Examples 1 to 3 and comparative compound 1 shown below was observed with the naked eye at 25° C. For those samples that were solid at 25° C. the melting point was determined. The results obtained are shown in Table 1 below.

[Chem.5]

Comparative Compound 1

TABLE 1

| | Compound | State at 25° C. | Melting Point |
|---|---|---|---|
| Comp. Example 1 | comp. compound 1 | solid | 115° C. |
| Eval. Example 1 | compound No. 3 | liquid | — |
| Eval. Example 2 | compound No. 4 | solid | 54° C. |
| Eval. Example 3 | compound No. 8 | liquid | — |

It is seen from the results in Table 1 that, while the compound of Comparative Example 1 has a melting point of 115° C., the melting points of the compounds of Evaluation Examples 1-1 to 1-3 are lower than a half of the melting point of the comparative compound, with zero degree C. taken as a base. It is noteworthy that the compounds of Evaluation Examples 1-1 and 1-3 are liquid at 25° C.

As a result of the DSC analysis, the ruthenium compounds of the invention proved to have thermal stability of 250° C. or higher. Seeing that the ruthenium compounds of the invention are liquid at 25° C. or liquefied by slightly heating as can be seen from the results of Evaluation Examples 1-1 to 1-3, they prove able to maintain a liquid state stably. This indicates that the ruthenium compounds of the invention, when used as a chemical vapor growth material, are stably delivered in a liquid state and are introduced in the form of vapor to a substrate without undergoing thermal decomposition upon being vaporized.

It has thus been proved that the ruthenium compounds of the invention are suited for use as a material for thin film formation by chemical vapor growth techniques.

Evaluation Example 2—Evaluation of Hydrogen Reactivity

TG-DTA of compound Nos. 3, 4, and 8 prepared in Examples 1 to 3 and comparative compound 1 was conducted under the following conditions: 80 ml/min hydrogen; 20 ml/min argon; rate of temperature rise of 10° C./min; and a sample weight of about 10 mg; to determine the temperature at which the reaction between the compound being analyzed and hydrogen ended. The temperature at which the reaction with hydrogen ended was defined to be the temperature above the 50% weight loss temperature of the compound being analyzed and at which the weight loss of the compound for a temperature rise by 50° C. decreased to less than 0.5%. The results are shown in Table 2.

TABLE 2

| | Compound | Reaction End Temperature (° C.) |
|---|---|---|
| Comparative Example 2 | comparative compound 1 | 305 |
| Eval. Example 2-1 | compound No. 3 | 275 |
| Eval. Example 2-2 | compound No. 4 | 250 |
| Eval. Example 2-3 | compound No. 8 | 250 |

As can be seen from the results in Table 2, while the compound of Comparative Example 2 needs a temperature higher than 300° C. to end the reaction with hydrogen, all the compounds evaluated in Evaluation Examples 2-1 to 2-3 complete the reaction with hydrogen at temperatures lower than 300° C. In particular, the compounds of Evaluation Examples 2-2 and 2-3 complete the reaction with hydrogen at temperatures lower than the reaction end temperature of Comparative Example 2 by more than 50° C.

It has thus been proved that a thin film formation material containing the ruthenium compound of the invention, which reacts with a reactive gas typified by hydrogen at low temperatures, does not require heating to high temperatures in thin film formation and is therefore an excellent material for thin film formation featuring good productivity.

The invention claimed is:

1. A ruthenium compound represented by general formula (I):

wherein $R^1$, $R^2$, and $R^3$ each independently represent a straight or branched chain alkyl group having 1 to 5 carbon atoms, provided that the total number of the carbon atoms of $R^1$ and $R^2$ is 3 to 10.

2. The ruthenium compound according to claim 1, wherein $R^1$ and $R^2$ are each an ethyl group.

3. The ruthenium compound according to claim 1, wherein $R^1$ and $R^2$ are each an isopropyl group.

4. A material for thin film formation comprising the ruthenium compound according to claim 1.

5. A process for forming a thin film comprising vaporizing the material for thin film formation according to claim 4 and introducing the ruthenium compound-containing vapor into a deposition chamber having a substrate placed therein to cause the ruthenium compound to decompose and/or chemically react to form a ruthenium-containing thin film on the substrate.

6. A material for thin film formation comprising the ruthenium compound according to claim 2.

7. A material for thin film formation comprising the ruthenium compound according to claim 3.

* * * * *